United States Patent
Plant et al.

(10) Patent No.: US 7,682,024 B2
(45) Date of Patent: Mar. 23, 2010

(54) SACCADIC MOTION SENSING

(76) Inventors: Charles P. Plant, 179 Lockland Ave., Framingham, MA (US) 01701; William T. Denman, 417 Main St., Winchester, MA (US) 01890-2925; Craig A. McKeown, 900 NW. 17th St., Miami, FL (US) 33136; Kenneth C. Humphries, 4147 Arno Rd., Franklin, TN (US) 37064

( * ) Notice: Subject to any disclaimer, the term of this patent is extended or adjusted under 35 U.S.C. 154(b) by 1576 days.

(21) Appl. No.: 10/799,045

(22) Filed: Mar. 13, 2004

(65) Prior Publication Data

US 2004/0181168 A1   Sep. 16, 2004

Related U.S. Application Data

(60) Provisional application No. 60/454,256, filed on Mar. 13, 2003.

(51) Int. Cl.
*A61B 3/14* (2006.01)
(52) U.S. Cl. .................. 351/209; 351/210; 351/221; 606/10; 606/12; 600/558
(58) Field of Classification Search ............. 351/200, 351/209–211, 216, 221; 606/2–5, 10–14, 606/18, 19; 600/558, 585; 382/117, 254
See application file for complete search history.

(56) References Cited

U.S. PATENT DOCUMENTS

| | | | | |
|---|---|---|---|---|
| 4,889,422 A | | 12/1989 | Pavlidis | |
| 5,341,181 A | * | 8/1994 | Godard | 351/210 |
| 5,410,376 A | * | 4/1995 | Cornsweet et al. | 351/210 |
| 5,422,690 A | * | 6/1995 | Rothberg et al. | 351/209 |
| 5,537,162 A | * | 7/1996 | Hellmuth et al. | 351/206 |
| 5,886,767 A | * | 3/1999 | Snook | 351/212 |
| 5,966,197 A | * | 10/1999 | Yee | 351/210 |
| 6,283,954 B1 | | 9/2001 | Yee | |
| 6,302,879 B1 | * | 10/2001 | Frey et al. | 606/12 |
| 6,322,216 B1 | * | 11/2001 | Yee et al. | 351/210 |
| 6,467,905 B1 | * | 10/2002 | Stahl et al. | 351/202 |
| 6,626,894 B2 | | 9/2003 | Frey | |
| 6,626,895 B2 | | 9/2003 | Frey | |
| 6,626,898 B2 | | 9/2003 | Frey | |
| 6,652,458 B2 | | 11/2003 | Blazey | |
| 6,666,857 B2 | * | 12/2003 | Smith | 606/12 |
| 6,702,757 B2 | | 3/2004 | Fukushima et al. | |
| 6,726,680 B1 | * | 4/2004 | Knopp et al. | 606/12 |
| 7,113,170 B2 | * | 9/2006 | Lauper et al. | 345/158 |
| 2002/0013573 A1 | | 1/2002 | Telfair | |
| 2002/0013577 A1 | | 1/2002 | Frey | |
| 2002/0051116 A1 | | 5/2002 | Van Saarloos et al. | |
| 2002/0188219 A1 | | 12/2002 | Suchard | |
| 2005/0110950 A1 | | 5/2005 | Thorpe et al. | |

FOREIGN PATENT DOCUMENTS

WO    WO 99/18842 A    4/1999

* cited by examiner

*Primary Examiner*—Loha Ben
(74) *Attorney, Agent, or Firm*—Law Office J. Shedd; Jill C Shedd

(57) ABSTRACT

A saccadic motion detector comprised an optical system that focuses light reflected or emitted from the subject's eye onto an optical navigation chip, which connects to circuitry configured to convert analog light from the eye to digital representations motion of the eye, including saccadic eye movement.

15 Claims, 3 Drawing Sheets

SACCADIC MOTION SENSING

CROSS-REFERENCE TO RELATED ACTIONS

This non-provisional patent application claims the benefit of U.S. Provisional Application No. 60/454,256 filed Mar. 13, 2003.

FIELD OF THE INVENTION

The invention relates to motion detection of the eye, and in particular, to saccadic eye movements.

BACKGROUND OF THE INVENTION

Day surgery under general anesthesia is now common and continues to grow in popularity owing to patient convenience and medico-economic pressures. Perioperative care improvements have allowed surgeons to perform more invasive day-surgical procedures. Additionally, the availability of drugs, such as propofol and remifentanil, has improved anesthesia care for more extensive surgeries. After surgery, especially day surgery, patients usually desire discharge as soon as possible.

Saccadic eye movements can be used to monitor recovery from general anesthesia. Indeed, evaluation of saccadic eye movements is more sensitive than choice-reaction tests in detecting the residual effects of anesthesia. Also, evaluation of saccadic eye movements is more reliable than subjective state-of-alertness tests, such as the visual analogue score for sedation, owing to the tendency for subjects to underestimate their impairment.

Eye movements may be affected by alcohol or other drugs. The effects of alcohol on saccadic eye movements were reported over three decades ago. Indeed, in field sobriety tests, law enforcement officers are trained to recognize end-point nystagmus that can be elicited by having the subject gaze laterally to the extreme. At least one study has described the change in saccadic eye movements as a measure of drug induced central nervous system (CNS) depression caused by Valium (diazepam). In the mid-1980s, the effects of barbiturates, benzodiazepines, opiates, carbamazepine, amphetamine and ethanol on saccadic eye movements were observed using a computer system coupled to a television monitor that provided visual stimulation for the subject, and an electrooculogram that measured eye movements. Not surprisingly, barbiturates, benzodiazepines, opiates, carbamazepine, and ethanol reduced peak saccadic velocity while amphetamine increased it. Saccadic eye movements have been studied in subjects who were given nitrous oxide or isoflurane. No significant differences were found between air and nitrous oxide. However, isoflurane caused significant diminution of mean saccadic peak velocity. In contrast, there was little effect caused by nitrous oxide or isoflurane on subjective assessment, assessed by subject's reporting of odor, tiredness, drowsiness, sleepiness, or nausea. It has also been reported that both cyclopropane and halothane depressed peak velocity of saccadic eye movements in a dose-dependent fashion. Peak saccadic velocity returned to baseline within 5 minutes after discontinuation. As found with isoflurane, no significant difference was found between halothane, cyclopropane, and air in subjective assessment of impairment. In a separate placebo-controlled trial, a diminution was found in peak saccadic velocity after propofol infusion. A study of the effect of isoflurane on some psychometric measurements showed that isoflurane diminished peak saccadic velocity, increased choice reaction time, and decreased visual analogue scores for sedation, but did not change the critical threshold for flicker fusion. It has been suggested that a combination of peak saccadic velocity, percentage error and choice reaction time would be a potentially useful battery of tests to assess recovery from anesthesia.

More recently, the effect of isoflurane has been studied regarding (1) saccadic latency and (2) a countermanding task. In a saccadic latency test, a moving target comprising a light-emitting diode was displayed on a screen. The latency of eye movements after target movements was measured, and was found to increase with anesthetic dose. In the countermanding task, which requires a higher level of conscious performance, the subject was asked to voluntarily suppress gaze movement to the target. Again, anesthetic increased the latency of response. Both tasks were equally impaired at sub-anesthetic concentrations of isoflurane.

Emergence from anesthesia and return of cognitive function is faster using a combination of propofol and remifentanil as compared to desflurane and sevoflurane. Hence, the propofol-remifentanil combination has become increasingly popular among anesthesiologists.

Measuring saccadic eye movements is a reliable and sensitive method to assess residual effect general anesthesia. Existing methods of measuring saccadic eye movement include electro-oculography (EOG) and use of high-speed video.

EOG has long-been available, and is probably the most widely used method for measuring horizontal eye movement in the clinic setting. EOG is a technique that can record a wide range of horizontal eye movements (±40°) but is less reliable for vertical eye movements. EOG uses the fact that a normal eyeball globe is an electrostatic dipole. The cornea is 0.4-1.0 mV positive relative to the opposite pole. Cutaneous electrodes are placed on both sides of the orbit. The potential difference recorded depends on the angle of the globe within the orbit.

Video detection of saccadic eye movements has been used. Normal video frame rates, however, of 30 Hz are slow relative to the high-speed saccade. Eye tracking devices, however, do exist for tracking this high-speed event using video speeds of 240 Hz or more. Currently the highest available is 480 Hz. These devices are typically complicated and delicate, range in price from $10,000 to $40,000, and often use high-speed cameras, precise delicate optics, image processors, image analysis software, and timed illumination sources to measure saccades.

SUMMARY OF THE INVENTION

The invention provides many advantages as elaborated below. In particular, objective measures of central nervous system impairment upon recovering from anesthesia may be obtained. The invention allows the detection of saccadic motion and analysis thereof. The invention provides a means to mass produce a low-cost, simple-to-use, battery-powered device that is portable and durable. Parameters obtained in saccadic motion detection can be used to provide objective measures of impairment or recovery due to drugs such as benzodiazepines, ethanol (alcohol), narcotics, barbiturates, amphetamines, anesthetic gases, and/or toxins, like mustard agents or sarin. Further, parameters obtained in saccadic motion detection can be used to provide objective measures of, dementia, delirium, psychosis, mania, attention deficit, depression, fatigue, intoxication, and/or sedation. Humans and animals recovering from anesthesia can be monitored prospectively to chart their progress. Parameters obtained in saccadic motion detection are helpful in diagnosing neurological defects, such as stoke or Alzheimer's disease. Such testing may supplant blood, urine, and/or hair sample testing owing to increased sensitivity. Indeed, such testing provides economic benefit over extant testing modalities. In the case of medical practitioners, such testing is safer and less invasive in that phlebotomies and/or urine specimens are obviated. The invention provides a means for automated testing, and simplifies personnel training. Parameters obtained in saccadic motion detection can be reported frequently and/or in near real-time, for example minute by minute. The invention may obviate the need for test sample, such as urine, and thereby may reduce the risk of sample mishaps. Since many physiologic systems affect saccadic performance, a plethora of conditions can be diagnosed. And since saccade generation is principally an unconscious act, the technique is difficult to fool or defeat, indeed, it may work in non-cooperative subjects, for example animals. The following figures, detailed description, and claims further expound the advantages of the invention.

DETAILED DESCRIPTION OF PREFERRED EMBODIMENTS

Figure 1:
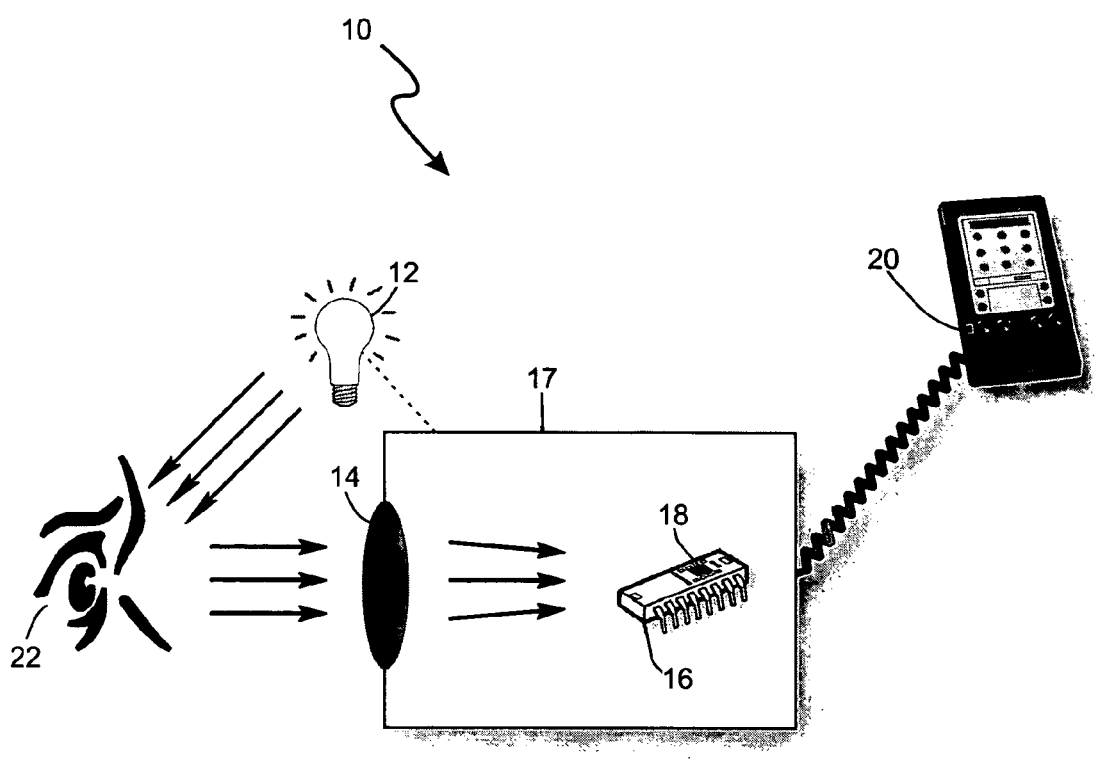
FIG. 1 is the system for measuring saccadic motion.

The embodiments herein provide techniques for measuring saccade motion. These metrics can be used for diagnosing corresponding conditions based on a database of saccadic motion baselines. Light emitted of reflected from the subject's eye is focused through an aperture to an optical navigation chip. This chip employs a charge-coupled device (CCD) array to measure the incoming image. The analysis of pixels of light allows the chip to report eye position. These measurements occur rapidly at frequencies of 1200 times per second or more, and in some cases around 6000 times per second. Sequential states of the CCD array are compared to determine magnitudes and directions in two dimensions, up-down left-right. The chip reports the magnitude of movement as a proportional integer whose sign indicated directions. Two integers are reported, one for each dimension. This information is further processed to determine angular position, rates and accelerations of the eye. These parameters are compared to standard rates for known conditions to aid with diagnosis. For example, a subject recovering from anesthesia will have parameters consistent with drug-impairment, fatigue, or intoxication. The system may predict the condition associated with the parameters seen. Other embodiments are also intended as follows:

Referring to FIG. 1, a saccadic eye movement detection and analysis system 10 includes a light source 12, an optical system with lens, 14; light sensor 16 comprised of a photosensitive array 18; and a data processor 20. The system 10 is configured to detect and analyze saccadic motion of the eye 22. The lens 14 and the light sensor 16 are mounted to housing 17, depicted here via a black rectangle. The light source 12 can also be mounted to housing 17. The system 10 uses optical navigation chip technology to determine eye position and motion. The sensor 16 can be connected to the processor 20 for data transmittal, which can be achieved via a universal serial bus (USB) wire or other communications connection, such as 802.11 wireless networks. The processor 20 can be any of a variety of devices, including a laptop computer or a personal data assistant (PDA), as depicted. The system 10 preferably can be of a size and weight that is readily portable, which for example could be handheld. Depending on features the system 10 could weigh less than about 1 to 2 pounds, and have dimensions of about 1×3×9 inches so that it approximates the size of extant ophthalmoscopes. The light source 12 can be outside the spectrum visible to humans. CCDs can "see" in the near infrared, which is the basis for television remote controls. The light source 12 can be ambient, or a light bulb, or other devices; but, a light emitting diode (LED) has the advantage of a wide variety of intensities and wavelengths. This makes it possible to illuminate the subject's eye in the near-infrared and outside the visible spectrum.

The lens 14 focuses light reflected, emitted and/or scattered from, e.g., the conjunctiva, sclera, vitreous, retina, limbus, and/or cornea. The optical apparatus 14 is located near the subject's eye 22, but preferably does not touch the eye. Light from a patch on the surface of the eye 22 is brought to focus on the sensor 16. The lens 14 can also be configured to focus light reflected by the entire width and height of the eye 22 to the entire length and width of the photosensitive array, or more commonly, a representative patch of the corneal surface is focused on the entire length and width of the photosensitive array 18.

The light sensor 16 is preferably an optical navigation semiconductor chip also containing the photosensitive array 18. For example, the sensor 16 could be model ADNS-2620 made by Agilent Technologies™ of Palo Alto, Calif. The ADNS-2620 is a small form-factor optical mouse sensor, which can be produced cheaply in high volume, and is the basis of many computer non-mechanical mice tracking engines. Using this optical navigation technology, changes in position are detected by optically acquiring sequential surface images (frames) and mathematically determining the direction and magnitude of movement. There are no moving parts, so precision optical alignment is not required, thereby facilitating high volume assembly. The array 18 comprises a two-dimensional set, e.g., 16 by 16 to provide 256 pixels of captured light. The pixels of the CCD measure intensity of light received by each element. The CCD array is clocked and read at regular intervals. The charge produced by the received light is thereby emptied of their stored charge and reset for the next round of light capture. The speed of a CCD array allows for rates from about 1200 Hz to about 6000 Hz or more. These frequencies are exemplary only, and reflect the optical navigation semiconductor chips now available, but indeed, other capture frequencies may be used, including frequencies less than 1200 Hz, as well as more than 6000 Hz.

The system 10 can use an optimization schema based on mathematical cross correlations of sequential frames to determine movement. Preferably the optimization schema is deterministic and finite rather than convergent and potentially infinite. The chip 16 analyzes successive states of the array, at intervals from about $\frac{1}{6000}$th of a second to about $\frac{1}{1200}$th of a second, to determine whether a significant difference in the values detected by elements of the array 18 exists. If there is a significant change, the system invokes an optimization schema as follows. Fractions of pixels can be ignored or rounded. If the image was perfectly random from frame to frame, the system would generate random numbers from the set $\{-7, -6, -5, -4, -3, -2, -1, 0, 1, 2, 3, 4, 5, 6, 7\}$ independently in the X and Y channels. If there is no movement, then the chip 16 can output nothing, and can so indicate to processor 20. If a significant change has occurred, then the chip 16 determines two values indicative of the change. These two values represent the magnitude and direction of the changes in the two dimensions of the array 18, e.g., x and y. For example, if the array 18 is a 16 by 16 array, then the chip preferably can output two values each ranging between −7 and +7, the number indicating the magnitude of the change and the sign (+/−) indicating the direction. This processing preferably occurs on the chip 16 so that a host computer 20 is spared the notorious and computationally intense problem of image recognition. The chip 16 is preferably silent when there is no change and when movement occurs data is reported in standard USB format at 1200 times per second or more. The technology is precise and high-speed, making it well-suited for monitoring eye motion. In the case of computer mice, the data are reported as a rapid series of integer up-down, left-right data that is processed to give the sensation of fluid, continuous motion of the mouse pointer on the user's monitor.

To characterize eye motions including saccades, the data can be processed by an optimization schema using sequential cross-correlations. For example, the array 18 may be a 16 by 16 array of elements. To determine the x-axis data (e.g., left-right), the columns (y-axis data) are collapsed by combining (e.g., adding, averaging or by weighted averaging) the values of all the elements in each column to produce a single row of x-axis data comprised of a set of 16 values. This is done for sequential frames from the array 18 and data can be accrued over time. Then, two single-row sets are compared (cross-correlated) to determine the most likely direction and magnitude shift of set 1, this cross-correlation occurring preferably against an antecedent or just antecedent set, so as to determine which of set 1 can be shifted to "best fit" set 2. For a 16 by 16 array, and thus a 16-element row, set 0 can be shifted up to 7 elements in either direction, thus yielding x data in the range of −7 to +7. (−7 to +7 is 15 states, so one pixel can be wasted.) The same algorithm is preferably applied to determine the y data, i.e., collapsing rows into a single column and cross-correlating single columns of data. The advantage of this algorithmic approach is that no traditional image processing is necessary, but texture movement or "flow" is detected.

The processor 20 can also include software for processing, scoring against standards, and presenting the data in a physiologically meaningful format. The software can also address issues such as internal validity or statistical significance. Motion information sensed and/or determined by the sensor 16 and/or the processor 20 can be selectively presented. For example, motion information can be filtered to eliminate confounding motions and/or artifact motions that are of non-saccadic, for example turning and or bobbing of the subject's head. Saccadic motion information can be presented against preexistent data representing conditions associated with the saccadic motion abnormalities. Accordingly, the software can predict intoxication, fatigue, and/or anesthesia, etc. The software can report similarities of saccadic motion matches, and the likelihood of being correct for the corresponding condition, the so-called "positive predictive power." Similarly, the software can rule-out intoxication, fatigue, and/or anesthesia, etc., and then report and the likelihood of being correct, the so-called "negative predictive power." The system 10 can be adapted for use by law-enforcement personnel including patrol officers responsible for field sobriety tests. There, the system could provide an objective indication of whether the subject is intoxicated, and provide a quantitative score of intoxication useful extemporaneous but reliable and unbiased decision-making in the field. On the other hand, the system could report that the subject is normal.

Figure 2:
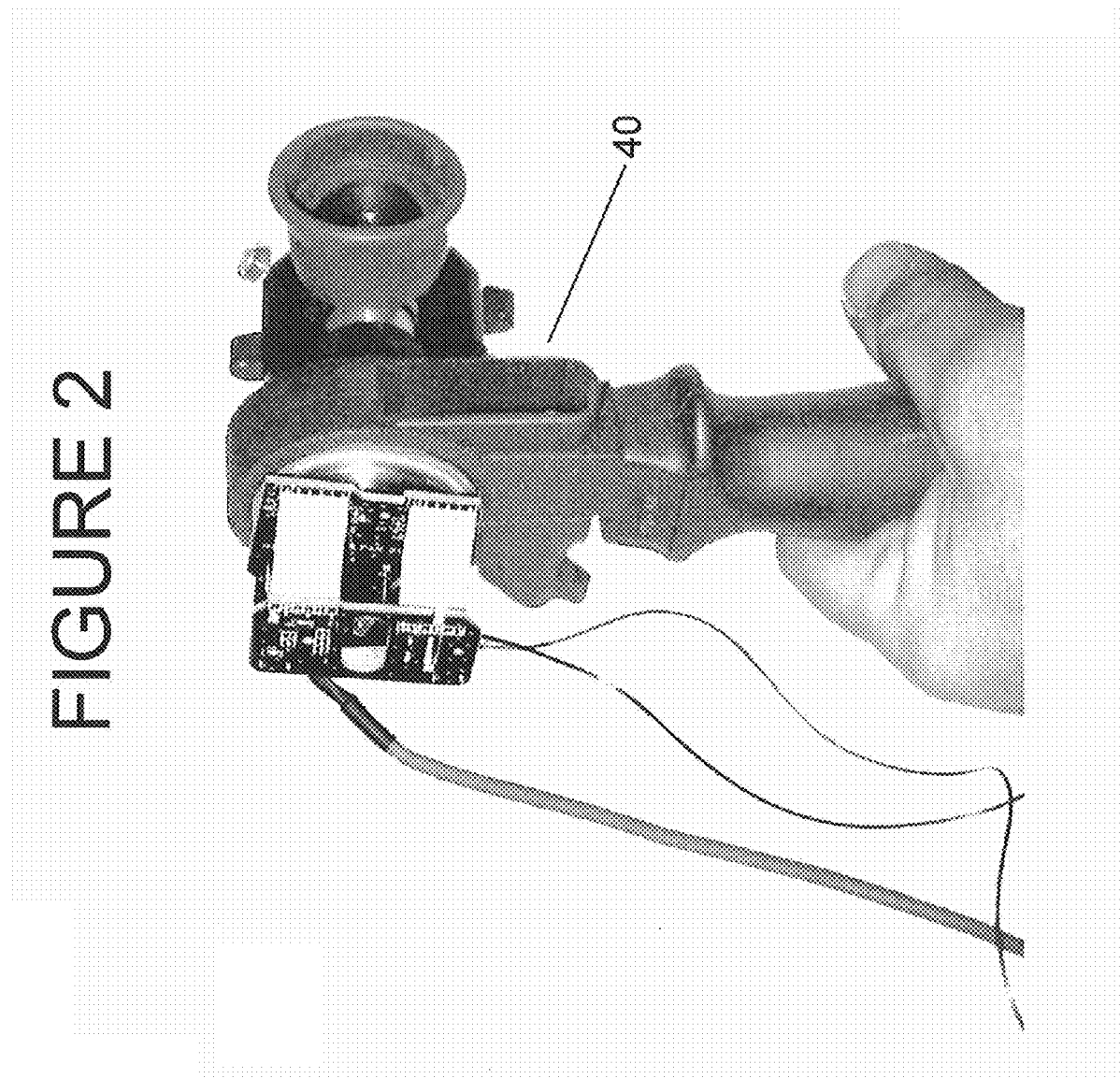
FIG. 2 is a prototype of a saccadic motion detector.

FIG. 2 is an early prototype of the device. The device 40 is handheld and includes an LED on a tether for illumination, a focusing apparatus for the subject and the examiner, and a light sensor mounted on a printed circuit board. Later models will likely omit the examiner view port. The handheld device 40 is small and portable. The handle provides for easy grasping. The device 40 is relatively lightweight, but can be made more so in follow-on models. The device can be battery operated thus increasing portability. The device can be connected to the computer 20 to increase features; but, the device 40 can be used as a stand-alone device, store its measured data, and then transfer the stored data to the computer 20 at a convenient time. The link between device 40 and computer 20 can be wireless, for example via an 802.11 protocol, including BlueTooth. The system 10 is also adaptable. The software and/or hardware and/or firmware of the light sensor 16, the computer 20, and/or of the device 40 can be upgraded to adapt to new technologies, new associations of saccadic motion to conditions, etc.

Figure 3:
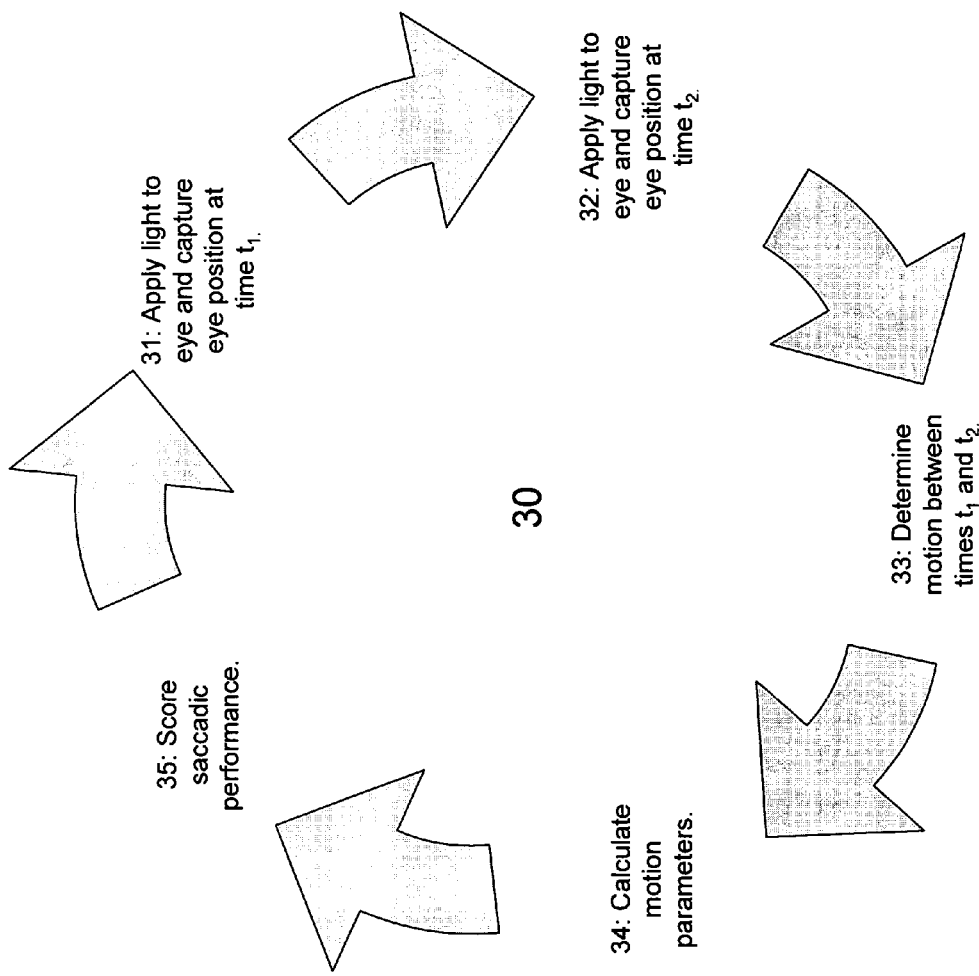
FIG. 3 is the information process cycle in the system for measuring saccadic motion.

FIG. 3 depicts the exemplary processing steps that can be used for categorizing saccadic eye movement using the system 10, but process 30 can be different by having stages added, removed, and/or rearranged.

At step 31, light is applied to the eye and the reflected or emitted light is captured to determine eye position at time $t_1$. The light source 12 can be controlled and turned on at time $t_1$ by processor 20 or manually by an operator, or the light source can be ambient. The light illuminates the subject's eye 22, when the examiner or operator places the housing 17 in front of the eye 22. Light reflected or emitted from the eye 22 and is captured by the sensor 16 through the array of photosensitive elements 18 to capture the eye position at time $t_1$.

At step 32, light is applied to the eye and the reflected or emitted light is captured to determine eye position at time $t_1$. The light source 12 can be controlled and turned on a second time at time $t_2$ by processor 20 or manually by an operator, or the light source can be ambient. Light reflected or emitted from the eye 22 and is captured by the sensor 16 through the array of photosensitive elements 18 to capture the eye position at time $t_2$.

At step 33, the motion between times $t_1$ and $t_2$ can be determined. The magnitude and direction of differences in eye position between the image captured at the first time $t_1$ and the second time $t_2$ are determined taking into account eye geometry and optical system magnification. As discussed above, the sensor 16 can collapse the intensities in x- and y-dimensions for sequential images for rapid comparison of the collapsed values to predict the likely motion that occurred between the two images. Said another way, the sensor 16 can determine the magnitude and direction of shifts to the x- and y-values of the first image that will cause the collapsed intensities of the first image from time $t_1$ to best match the collapsed intensities of the second image from time $t_2$.

At step 34, the system can calculate motion parameters based on the distance shifted. The times $t_1$ and $t_2$ can be sequential times of the sensor 16, such that consecutive clockings and readings from sensor 16 are obtained, and motion can be reported at all clockings regardless of shift magnitudes, or motion can be reported only when there is a significant shift between consecutive clockings. The times $t_1$ and $t_2$ can, however, be nonconsecutive times separated by one or more clock cycles. For example, the second time $t_2$ can correspond to a clock cycle where the light sensor 16 determines a significant change in the captured image, which achieves a predefined threshold amount relative to the image captured at the first time $t_1$, and thus does not necessarily occur between consecutive clock cycles.

At step 35, saccadic performance can be scored against previous measures of the same subject, or, saccadic performance can be scored against previous measures of the another subject, or, saccadic performance can be scored against previous measures of the others subjects in aggregate form using population statistics, where the comparison subject or group can be a population of normal or abnormal subjects, where the abnormal subjects are representative of know disorders, diseases, conditions, or variants. The processor 20 uses the information obtained from light sensor 16 regarding eye movement parameters, to calculate or otherwise determine, by for example, using a lookup table or a polynomial curve fit that maps saccadic performance parameters to a known database. The processor can determine various parameters such as velocity, maximum velocity, acceleration, latency, etc. associated with the eye movement. Processor 20 can categorize and where appropriate can quantify conditions associated with the subject's eye movement parameters. The processor 20 can relate the determine parameters to known relationships between parameters and conditions in an attempt to categorize the condition associated with the subject's movement parameters, choosing among various abnormal states, such as, anesthetized, intoxicated, fatigued, delirious, manic, attention deficit, etc. If the exact condition is indeterminate, a "rule-out" list can be formulated to suggest avenues of further investigation. The processor 20 can also help quantify conditions, heavily sedated versus lightly sedated, or is the anesthesia "on board" now sufficient for the planned procedure, or is the subject "legally" intoxicated, etc. The processor 20 can inform the examiner using various modalities, such as lights or displays (LCDs), monitors or indicators or enunciators including audible indicators using tones, beeps, chimes, or bells, etc., that can indicate the subject's condition and other information to an operator of the system 10. For example, the processor 20 may indicate that the subject's condition is normal, impaired, anesthetized, intoxicated, fatigued, delirious, manic, attention deficit, depressed, or manic. The impaired condition can be caused by one or more substances such as benzodiazepines, ethanol (alcohol), narcotics including heroine and cocaine, barbiturates, and amphetamines including "crystal-meth". Although presently in many cases, the system cannot identify the exact substance present, it can determine whether a stimulant, such as amphetamine, or a depressant such as alcohol is present; but, in the case of opiates, overly-constricted pupils is quite specific for opiate use/abuse. As the technology advances, the system may be able to determine the exact substance present in most cases.

The process 30 can be customized so that the invention can enjoy a wide variety of applications. The invention can be used for objective measurement of recovery from anesthesia after a medical/surgical procedure. The invention can be applied to a variety of medical and non-medical disciplines, such as anesthesia, emergency medicine, neurology, psychiatry, critical care, ophthalmology, geriatrics, forensic medicine, alcohol intoxication, drug intoxication, drug compliance, impairment due to fatigue, etc.

These areas may find numerous specific uses for the invention. For anesthesiologists and/or intensivists may find use for the invention, e.g., in the post anesthesia care unit (PACU), for critical care (e.g., ICU), in pain management clinics, in operating rooms, in hospitals generally, for diagnosing dementia vs. delirium, and for pre-op screening including substance abuse. Neurologists may use the invention for diagnosing and/or monitoring conditions such as multiple sclerosis, myasthenia gravis, ALS, Alzheimer's, stroke (CVA), time course of brain disease, and substance abuse. Ophthalmologists and otolaryngologists (ENTs) may use the invention for monitoring and/or diagnosing motor vs. visual defects, strabismus and nystagmus, vertigo and vestibular function, and trauma. Psychiatrists may use the invention for diagnosing and/or monitoring dementia vs. delirium, mood disorders vs. psychosis, and substance abuse. Emergency room personnel may use the invention for diagnosing and/or monitoring delirium vs. dementia, stroke (CVA), trauma, environmental toxin (including terrorism toxin) influence, and substance abuse. Any of these or other people may find further uses for the invention, and these uses noted are exemplary only and not limiting.

The invention can be applied to needs in the hospital, clinic and day surgery center, forensic testing and law enforcement and public safety agencies. The invention can also be useful for lay applications, for example for commercial, job site, or home use by parents or guardians. The invention may be used for numerous forensic applications in the field or as a screening tool, at airports for example. Manufacturers handling explosives or flammable materials, or whose personnel use heavy equipment, can use the invention as a safety screen to detect intoxication of employees. Mission critical enterprises such as financial and accounting institutions or employers of computer programmers or operators may likewise use the invention, e.g., for detecting intoxicated employees. For similar reasons, and others, transportation providers such as airline carriers, bus operators, car rental companies, taxi/limousine/livery companies, ship operators, etc. may also use the invention. Other screening and testing applications are also within the scope of the invention, and the list will grow as society embraces the technology.

Other embodiments are within the scope and spirit of the appended claims. As accessories to the invention are developed, more functions described above can be implemented using software, hardware, firmware, hardwiring, or combinations of any of these. The functions described can be subserved by various system components, for example, functions described above being performed in the chip 16 can be partially or entirely performed in the processor 20, and functions described above being performed in the processor 20 can be partially or entirely performed in the chip 16. Other optical navigation semiconductor chips can be used to detect and transduce light from the eye. Also, while the computer 20 is shown in FIG. 1 as a personal digital assistant (PDA), other forms of computing devices are acceptable, such as personal desktop or laptop computers, etc. And while the computer 20 may be hardwired, a wireless connection to the device can be used, using for example Bluetooth or IEEE 802.11 protocols. Further, embodiments of the invention may not use a focusing apparatus light the apparatus 14 shown in FIG. 1. Light reflected from the eye 22 could be captured by the light sensor 16 without having been focused on the sensor 16.

What is claimed is:

1. A saccadic-motion detection device comprising an optical system for focusing light reflected and/or emitted from a subject's eye directly onto an optical navigation chip, said optical navigation chip comprising a solid state semiconductor whereby the solid state semiconductor contains a photo sensitive imaging array which is configured for recording the focusing light reflected and/or emitted from the subject's eye and for measuring saccadic eye movement.

2. The saccadic motion detection device of claim 1, wherein the optical navigation chip directly converts the incident light into digital representations of the movement or position of the eye, or both.

3. The saccadic-motion detection device of claim 1, wherein the optical navigation chip is configured to determine the rate of movement of the eye.

4. The saccadic-motion detection device of claim 1, wherein the optical navigation chip is configured to determine angular position, speed, and/or acceleration of the eye.

5. The saccadic-motion detection device of claim 4, wherein the optical navigation chip is configured to compare the value of position, speed, and/or acceleration with a table associating known or standard conditions to those values determined from the subject's eye.

6. The saccadic-motion detection device of claim 4, wherein a condition of the eye can be reported among known conditions for normal or impaired conditions, due to at least one of intoxication, fatigue, dementia, delirium, psychosis, attention deficit, hyperactivity, depression, or mania.

7. The saccadic-motion detection device of claim 6, wherein the condition of intoxication can be determined that is caused by drugs, such as benzodiazepines, ethanol (alcohol), barbiturates, narcotics, narcotic mixtures, and amphetamines.

8. The saccadic-motion detection device of claim 1, wherein the optical navigation chip is configured with the capability to provide position or motion information at greater than 1200 times per second.

9. The saccadic-motion detection device of claim 1, wherein the optical navigation chip is configured with the capability to provide position or motion information at between about 1200 and about 6000 times per second.

10. The saccadic-motion detection device of claim 1, wherein a handheld mechanical frame is attached to the optical system and the optical navigation chip.

11. The saccadic-motion detection device of claim 1, wherein a source of light, said source of light being outside the visible spectrum for humans, is configured to be attached near the subject's eye so that the reflected light is received by the optical system.

12. The saccadic-motion detection device of claim 1, wherein the optical navigation chip contains an array of charge coupled devices (CCDs).

13. The saccadic-motion detection device of claim 1, wherein a subject is a creatures capable of saccadic eye motion, which includes humans and other animals.

14. A system for detecting saccadic eye movement comprising a motion transducer and, an optical apparatus configured to focus light received from a subject's eye directly onto the motion transducer, which then provides at least one indication of saccadic eye motion over a discrete interval of time.

15. The system of claim 14 further comprising a light source to illuminate the subject's eye, and and a housing for supporting all components of the system for ready portability.

* * * * *